(12) United States Patent
Ronan et al.

(10) Patent No.: US 12,178,437 B2
(45) Date of Patent: Dec. 31, 2024

(54) MEDICAL DEVICE FOR DILATING AN ENDOVASCULAR LUMEN

(71) Applicant: CLEARSTREAM TECHNOLOGIES LIMITED, Enniscorthy (IE)

(72) Inventors: Allan Ronan, Enniscorthy (IE); Lauren Keogh, London (GB); Ciaran Giles, Enniscorthy (IE)

(73) Assignee: CLEARSTREAM TECHNOLOGIES LIMITED (IE)

( * ) Notice: Subject to any disclaimer, the term of this patent is extended or adjusted under 35 U.S.C. 154(b) by 0 days.

(21) Appl. No.: 18/014,213

(22) PCT Filed: Jul. 3, 2020

(86) PCT No.: PCT/EP2020/068805
§ 371 (c)(1),
(2) Date: Jan. 3, 2023

(87) PCT Pub. No.: WO2022/002413
PCT Pub. Date: Jan. 6, 2022

(65) Prior Publication Data
US 2023/0190274 A1    Jun. 22, 2023

(51) Int. Cl.
*A61B 17/34*    (2006.01)
*A61B 17/12*    (2006.01)
*A61M 25/04*    (2006.01)
*A61M 29/02*    (2006.01)
*A61F 2/01*    (2006.01)

(52) U.S. Cl.
CPC ............. *A61B 17/12* (2013.01); *A61M 25/04* (2013.01); *A61M 29/02* (2013.01); *A61F 2002/016* (2013.01)

(58) Field of Classification Search
CPC .................. A61M 29/00; A61M 29/02; A61M 2029/025; A61B 17/3417; A61B 17/0206; A61B 17/02; A61B 1/32
See application file for complete search history.

(56) References Cited

U.S. PATENT DOCUMENTS 3,667,474 A * 6/1972 Lapkin .................. A61M 29/02
                                                                606/198
4,585,000 A * 4/1986 Hershenson .......... A61M 29/02
                                                                604/109
5,527,282 A    6/1996 Segal
(Continued)

FOREIGN PATENT DOCUMENTS

CN    111097095 A    5/2020

*Primary Examiner* — Erich G Herbermann
(74) *Attorney, Agent, or Firm* — Dickinson Wright PLLC; Andrew D. Dorisio (57) ABSTRACT

A medical device (10) for dilating an endovascular lumen and having a collapsed configuration and an expanded configuration, the medical device comprising a stem (20) extending along a longitudinal axis of the device; a first plate (30) disposed partly around the stem (20); a second plate (40) disposed partly around the stem (20) angularly separated in a circumferential direction from the first plate (30); and an expansion mechanism (50) configured to move each of the first plate (30) and/or the second plate (40) radially outwardly when the medical device (10) is expanded from the collapsed configuration to the expanded configuration.

17 Claims, 7 Drawing Sheets

(56) References Cited

U.S. PATENT DOCUMENTS

| | | | |
|---|---|---|---|
| 5,713,907 A * | 2/1998 | Hogendijk | A61M 29/02 |
| | | | 606/198 |
| 5,855,565 A | 1/1999 | Bar-Cohen | |
| 5,989,263 A | 11/1999 | Shmulewitz | |
| 6,348,061 B1 | 2/2002 | Whitman | |
| 6,582,451 B1 * | 6/2003 | Marucci | A61B 17/29 |
| | | | 606/207 |
| 8,317,798 B2 * | 11/2012 | Lim | A61B 17/025 |
| | | | 606/90 |
| 8,579,907 B2 * | 11/2013 | Lim | A61B 17/025 |
| | | | 606/90 |
| 2002/0077531 A1 * | 6/2002 | Puchovsky | A61B 17/0206 |
| | | | 600/232 |
| 2011/0152823 A1 | 6/2011 | Mohiuddin | |
| 2018/0014879 A1 | 1/2018 | Whiteley | |
| 2018/0055634 A1 | 3/2018 | White | |
| 2019/0091045 A1 | 3/2019 | White | |

* cited by examiner

MEDICAL DEVICE FOR DILATING AN ENDOVASCULAR LUMEN

TECHNICAL FIELD

The present disclosure relates to a medical device for dilating an endovascular lumen and having a collapsed configuration and an expanded configuration, the medical device comprising a stem, a first plate, a second plate and an expansion mechanism, and a method of dilating an endovascular lumen.

BACKGROUND

Vascular calcifications are mineral deposits on the walls of arteries and veins. Highly calcified vessels can have serious consequences and can increase the risk of stroke or blood clots for a patient.

Such calcified vessel lesions are currently generally treated through endovascular dilation using a balloon dilatation catheter or a scoring balloon catheter. A balloon catheter uses an inflatable balloon at the distal tip of a catheter to enlarge a narrow opening or passage within a patient body. The deflated balloon catheter is positioned within the vessel then inflated to dilate the calcified vessel and deflated again in order to be removed.

Some highly calcified lesions are difficult to dilate using just a balloon and require a more focused force to dilate the lesion at safe inflation pressures. A scoring balloon such as the one disclosed in European Patent EP 3 367 935 B1 can be used. This scoring balloon further comprises a number of longitudinal scoring wires disposed on the radial outer surface of the balloon to provide a greater concentrated force against the calcified plaque at lower inflation pressures.

However, there are a number of downsides to using balloons catheters. They generally have a maximum diameter to which they can be expanded, meaning that physicians need to stock a large number of balloon sizes to treat different sized vessels. Specifically, non-compliant balloons often only expand to one specific diameter. Furthermore, the extent of expansion of a balloon is difficult to control, as the physician has to rely on the pressure applied to the balloon and the maximum diameter of the balloon to estimate how far the balloon will open. Balloon catheters can also suffer from slow inflation times and the need for introduction of a large volume of fluid.

In view of the above, there is a need for an improved medical device for endovascular dilations which allows a more accurate and focused application of force to the vessel wall to crack calcifications with minimal damage, if any at all, to the vessel wall. There is also a need for a medical device for endovascular dilations which eliminates balloon related complications.

Furthermore, there is a need for an improved medical device for endovascular dilations which allows the physician to accurately determine and control the extent of expansion of the dilation device and the force applied to the vessel wall.

A need also exists for an improved medical device for endovascular dilations which has a greater range of expansion to cover a large number of target vessels.

BRIEF DESCRIPTION OF THE DRAWINGS

To enable better understanding of the present disclosure, and to show how the same may be carried into effect, reference will now be made, by way of example only, to the accompanying drawings, in which.

DETAILED DESCRIPTION

In one aspect of the present disclosure, there is provided a medical device for dilating an endovascular lumen and having a collapsed configuration and an expanded configuration. The medical device comprises a stem extending along a longitudinal axis of the device, a first plate disposed partly around the stem, a second plate disposed partly around the stem angularly separated in a circumferential direction from the first plate. The medical device further comprises an expansion mechanism configured to move each of the first plate and/or the second plate radially outwardly when the medical device is expanded from the collapsed configuration to the expanded configuration.

In some embodiments this may result in a medical device which can provide a more accurate and focused application of force to a vessel wall when dilating an endovascular lumen.

Throughout this disclosure, the term 'endovascular lumen' may refer to the inside space within a blood vessel of the human or animal body. The 'endovascular lumen' may be, for example, an artery or vein.

Throughout this disclosure, the term 'collapsed configuration' of an element may refer to a configuration of the element which has a smaller radial extent than an 'expanded configuration' of the element.

Throughout this disclosure, an alternative term for the 'expansion mechanism' may be an 'actuator'.

Another alternative term for the 'expansion mechanism' may be a 'driver'.

Another alternative term for the 'expansion mechanism' may be a 'mover'.

Another alternative term for the 'expansion mechanism' may be an 'expander'.

The expansion mechanism may be a mechanically driven leverage mechanism.

In some embodiments, this may result in more accurate determination and control of the extent of expansion of the medical device and therefore more accurate determination and control of the force applied to the vessel wall by the device.

In some embodiments, this may result in a greater range of expansion of the device to cover a larger number of target vessels.

The medical device may be a balloon-free medical device. The expansion mechanism may be a balloon-free expansion mechanism.

The first plate may be connected to the stem using at least two connection struts.

The second plate may be connected to the stem using at least two connection struts.

Each of the first plate and the second plate may be connected to the stem using at least two connection struts.

In some embodiments, this may result in a simple mechanical leverage mechanism.

In some embodiments, this may result in a greater range of expansion of the device to cover a larger number of target vessels.

The expansion mechanism may be configured to move the first plate radially outwardly by moving the at least two connection struts relative to each other.

The expansion mechanism may be configured to move the second plate radially outwardly by moving the at least two connection struts relative to each other.

The expansion mechanism may be configured to move each of the first plate and second plate radially outwardly by moving the at least two connection struts relative to each other.

In some embodiments, this may allow simple and accurate control over the extent of expansion of the device.

The at least two connection struts may each comprise a first end and a second end. The first ends may be connected to the stem and the second ends may be connected to the plate.

The first ends may be rotatably connected to the stem. The first ends may be connected to the stem using a joint or hinge.

The second ends may be rotatably connected to the plate. The second ends may be connected to the plate using a joint or hinge.

The expansion mechanism may be configured to move the first ends of the at least two connection struts relative to each other to move the first plate radially outwardly.

The expansion mechanism may be configured to move the first ends of the at least two connection struts relative to each other to move the second plate radially outwardly.

The expansion mechanism may be configured to move the first ends of the at least two connection struts relative to each other to move each of the first plate and second plate radially outwardly.

In some embodiments, this may allow for simple and accurate control of expansion of the device through movement of the connection struts.

The at least two connection struts may comprise a first strut and a second strut.

The first end of the first connection strut may be fixed to the stem to restrict longitudinal movement of the first end relative to the stem.

The first connection strut may be able to rotate relative to the stem.

The first end of the second connection strut may be movably connected to the stem such that the first end can move longitudinally relative to the stem.

In some embodiments, this may result in expansion of the device being controllable through movement of the first end of the second connection strut.

The second connection strut may be able to rotate relative to the stem.

The expansion mechanism may be configured to move the first end of the first connection strut and the first end of the second connection strut towards each other to cause each of the first plate and/or the second plate to move radially outwardly when the medical device is expanded from the collapsed configuration to the expanded configuration The second plate may be disposed opposite the first plate.

The expansion mechanism may be configured to move the first plate and the second plate radially outwardly in opposite directions when the medical device is expanded from the collapsed configuration to the expanded configuration.

In some embodiments, this may result in a more uniform application of force on the vessel wall.

The expansion mechanism may comprise a thread on the surface of the stem. One of the at least two connection struts may be threadably connected to the stem.

Rotation of the stem may cause the at least two connection struts to move relative to one another.

In some embodiments, this may result in a small amount of torque being translated into a high-pressure radial force within the vessel.

In some embodiments, this may also result in highly accurate control over the expansion of the device and thus the force which is applied to the vessel wall.

Rotation of the stem in a first direction may cause the first plate and/or the second plate to move radially outwardly and the medical device to expand from the collapsed configuration to the expanded configuration.

Rotation of the stem in a second direction may cause the first plate and/or the second plate to move radially inwardly and the medical device to collapse from the expanded configuration to the collapsed configuration.

In some embodiments, this may result in simple collapsing and removal of the device from the endovascular lumen.

The expansion mechanism may comprise the stem. The stem may have a tubular member and a pull wire.

The pull wire may extend distally from the tubular member.

A first connection strut of the at least two connection struts may be connected to the tubular member.

A second connection strut of the at least two connection struts may be connected to the pull wire.

Pulling the pull wire may cause the at least two connection struts to move relative to each other.

In some embodiments, this may result in an expansion mechanism with simple yet accurate control over the extent of expansion.

Pulling the pull wire may cause each of the first plate and/or the second plate to move radially outwardly. Pulling the pull wire may cause the medical device to expand from the collapsed configuration to the expanded configuration.

The pull wire may be disposed within the tubular member.

The expansion mechanism may comprise a hydraulic actuator.

Actuation of the hydraulic actuator may cause the at least two connection struts to move relative to one another.

In some embodiments this may result in a medical device with an accurate means to apply a great force to the vessel wall.

Actuation of the hydraulic actuator may cause the first plate and/or the second plate to move radially outwardly. Actuation of the hydraulic actuator may cause the medical device to expand from the collapsed configuration to the expanded configuration.

The first plate may comprise at least one ridge disposed on the radial outside surface of the plate.

The second plate may comprise at least one ridge disposed on the radial outside surface of the plate.

The first plate and the second plate may each comprise at least one ridge disposed on the radial outside surface of the plate.

In some embodiments, this may result in a more focused force being applied to the vessel wall through the ridge.

In some embodiments, this may result in a greater force being applied to the vessel wall through the ridge or ridges. In some embodiments, this may result in less force being required to dilate the vessel wall.

The at least one ridge may extend longitudinally along the first plate.

The at least one ridge may extend longitudinally along the second plate.

The at least one ridge may extend longitudinally along each of the first plate and the second plate.

In some embodiments, this may result in a more focused force being applied to the vessel wall along the length of the plate.

The at least one ridge may extend circumferentially along the first plate and/or the second plate.

The at least one ridge may extend in diagonal or helix shape along the first plate and/or the second plate.

Each of the first plate and/or the second plate may comprise a second ridge.

The first plate may be curved around the longitudinal axis of the device.

The second plate may be curved around the longitudinal axis of the device.

Each of the first plate and the second plate may be curved around the longitudinal axis of the device.

In some embodiments, this allows a more uniform application of force. In some embodiments, this also reduces vessel damage.

The cross-sectional shape of the first plate may be the arc of a circular sector.

The cross-sectional shape of the second plate may be the arc of a circular sector.

The cross-sectional shape of each of the first plate and the second plate may be the arc of a circular sector.

In some embodiments, this allows a more uniform application of force. In some embodiments, this also reduces vessel damage.

The first plate may comprise a first radiopaque marker.

In some embodiments, this may result in more accurate location of the medical device under fluoroscopy.

The first radiopaque marker may be arranged to indicate the longitudinal extent of the first plate.

In some of the embodiments this may result in more accurate identification of the working surface of the medical device under fluoroscopy.

The first plate may comprise a second radiopaque marker.

The first radiopaque marker and the second radiopaque marker may be arranged to indicate the longitudinal extent of the first plate.

In some of the embodiments this may result in more accurate identification of the working surface of the medical device under fluoroscopy.

The second plate may comprise a first radiopaque marker.

The first radiopaque marker of the first plate and the first radiopaque marker of the second plate may be arranged to indicate the distance between the first and second plates.

In some embodiments, this may result in more accurate determination of the extent of expansion of the medical device under fluoroscopy.

The medical device may further comprise a catheter, configured to be disposed around the first and second plates when the medical device is in the collapsed configuration.

In some embodiments, this may result in a simple method of introduction and removal of the medical device from a blood vessel.

In a second aspect of the present disclosure, there is provided a method of dilating an endovascular lumen. The method comprises introducing a medical device in a collapsed configuration into the lumen. The medical device comprises a stem extending along a longitudinal axis of the device, a first plate disposed partly around the stem, and a second plate disposed partly around the stem opposite the first plate. The method further comprises actuating the plates to move outwardly and expand the medical device from the collapsed configuration to an expanded configuration.

In some embodiments, this may result in a method which can provide a more accurate and focused application of force to a vessel wall when dilating an endovascular lumen.

The stem may comprise a threaded surface. The actuating step may comprise rotating the threaded stem in a first direction.

The actuating step may comprise pulling a pull wire attached at a distal end of the device.

The actuating step may comprise actuating a hydraulic actuation mechanism.

Figure 1:
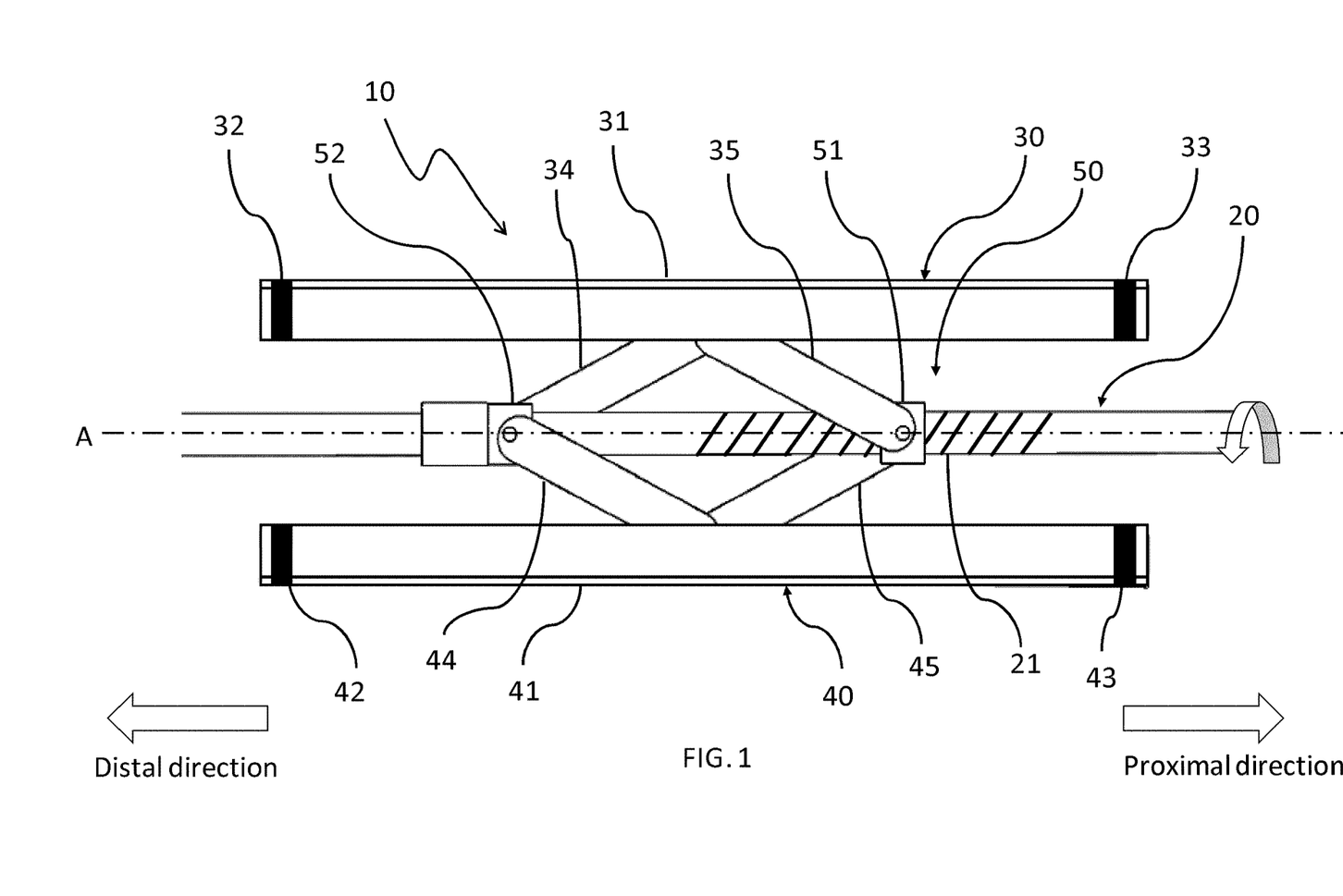
FIG. 1 shows a side view of one embodiment of a medical device for dilating an endovascular lumen in an expanded configuration according to the present disclosure.

FIG. 1 shows a side view of a medical device 10 for dilating an endovascular lumen in an expanded configuration according to an embodiment of the present disclosure. The medical device 10 comprises a central stem 20 which is arranged along a longitudinal axis A of the medical device 10. The medical device 10 further comprises a first plate 30 which is disposed partly around the stem 20 and a second plate 40 which is also disposed partly around the stem 20. The first plate 30 and the second plate 40 are arranged on opposite sides of the stem 20 such that they partly surround the stem 20 and are configured to move radially outwardly relative to the stem 20 when the medical device 10 is expanded from a collapsed configuration (described in more detail with reference to FIG. 2 below) to an expanded configuration, as shown in FIG. 1. The first and second plates 30, 40 can also move radially inwardly relative to the stem 20 when the medical device 10 is collapsed from the expanded configuration to the collapsed configuration.

The first plate 30 is curved around the longitudinal axis A of the device 100 and extends along the longitudinal axis A. The cross-sectional shape of the first plate 30 is the arc of a circle sector (as shown in FIG. 3). This shape allows the first plate 30 to better engage with a cylindrical vessel wall and prevents damaging the vessel wall when a force is applied by the first plate 30 on the vessel wall. The second plate 40 is also curved around the longitudinal axis A on the opposite side of the stem 20 and similarly extends along the longitudinal axis A. The second plate 40 has the same cross-sectional shape of the arc of a circle as the first plate 30. The first plate 30 and the second plate 40 may be made from a range of different materials which provide the required stiffness and durability such as, for example, stainless steel or other metals, polycarbonate, nylon or PEEK.

The first plate 30 comprises a first ridge 31 disposed on the radial outside of the first plate 30. Similarly, the second plate 40 comprises a second ridge 41 disposed on the radial outside of the second plate 40. The first ridge 31 and the second ridge 41 extend longitudinally along the length of the first plate 30 and the second plate 40, respectively. The ridges can be created during the plate casting process, by forming a ridge shape in the mould of the plate, for example, which keeps manufacturing steps low in number.

The ridges 31, 41 provide a focus point on the plates 30, 40 through which the force provided by the expanding plates 30, 40 can act on the vessel wall. This results in a higher force being applied at the point where the ridge 31, 41 come into contact with the vessel wall and means that highly calcified vessel walls can be more easily cracked using a lower overall force. The ridges 31, 41 allow the dilation of highly calcified vessels while causing minimal damage, if any at all, to the vessel wall.

To move the plates 30, 40 radially outwards, the medical device 10 comprises an expansion mechanism 50. Unlike known balloon dilatation catheters, where the inflation of a balloon is used as an expansion mechanism, the present device 100 relies on a mechanical leverage mechanism to move the first and second plates 30, 40 radially outwardly and inwardly. The expansion mechanism 50 comprises a first connection strut 34 and a second connection strut 35 which connect the first plate 30 to the stem 20, a third connection strut 44 and a fourth connection strut 45 which connect the second plate 40 to the stem 20, a moveable connector 51 and a fixed connector 52. The connection struts may be made from a similar material to the plates 30, 40, which has the required stiffness and durability. Examples of materials include stainless steel or other metals, polycarbonate, nylon or PEEK.

The first connection strut 34 is connected at a first end to the stem 20 through the fixed connector 52. The fixed connector 52 is attached to the stem 20 such that it cannot move longitudinally relative to the stem 20. However, the fixed connector 52 may rotate axially relative to the stem 20. The first end of the first connection strut 34 is connected to the fixed connector 52 with a hinge or joint so that the first connection strut 34 can rotate relative to the fixed connector 52 and the stem 20. A second end of the first connections strut 34 is connected to the radial inside of the first plate 30 with a joint or hinge so that the first connection strut 34 can rotate relative to the first plate 30.

The second connection strut 35 is connected at a first end to the stem through the moveable connector 51. The moveable connector 51 is attached to the stem 20 such that it can move longitudinally relative to the stem 20. The first end of the second connection strut 35 is connected to the moveable connector 51 with a hinge or joint so that the second connection strut 35 can rotate relative to the moveable connector 51 and the stem 20. A second end of the second connection strut 35 is connected to the radial inside of the first plate 30 with a joint or hinge so that the second connection strut 35 can rotate relative to the first plate 30.

The first connection strut 34 and the second connection strut 35 attach to the first plate 30 at the same point along the longitudinal axis A although they are radially spaced apart.

The second plate 40 is connected to the stem 20 in a similar manner as the first plate 30. Third connection strut 44 connects the second plate 40 to the stem 20 through fixed connector 52. Fourth connection strut 45 connects the second plate 40 to the stem 20 through movable connector 51.

Using mechanical connection struts in a mechanical expansion mechanism 50, allows for a greater range of expansion of the medical device 10 compared to, for example, a balloon dilatation catheter. One device 10 can therefore be used to treat a greater range of sizes of target vessels.

The stem 20 comprises a threaded portion where a thread 21 is disposed on the surface of the stem 20. The movable connector 51 has a corresponding inner thread and is threadably engaged with the threaded portion of the stem 20.

Rotation of the stem 20 in a first direction will therefore cause the movable connector 51 to move distally towards the fixed connector 52. This will cause a leverage action where the second ends of the connection struts, which are connected to the plates 30, 40, move radially outwards thereby pushing the first and second plates 30, 40 radially outwards. Rotation of the stem 20 in a first direction will expand the medical device 10 from a collapsed configuration to an expanded configuration. When the first and second plates 30, 40 engage a target vessel wall, further rotation in the first direction will increase the force which is applied to the inside of the vessel wall and cause the vessel to be dilated. Since the amount of rotation can be carefully controlled, for example, by a physician from outside the patient's body, the amount of force which is applied to the vessel wall can also be controlled very accurately and increased incrementally. This provides for a safer and more controlled manner of dilating a blood vessel and reduces instances of vessel trauma.

Once dilation of the vessel has been achieved, the stem 20 can be rotated in a second direction. Rotation of the stem 20 in a second direction will cause the movable connector 51 to move in a proximal direction away from the fixed connector 52. This will result in the first and second plates 30, 40 moving radially inwardly and the medical device 10 being collapsed from the expanded configuration to the collapsed configuration. When the medical device 10 is in the collapsed configuration, a catheter may be slid over the medical device to then remove the medical device 10 from patient's body.

The rotation of the stem 20 may be controlled by a physician outside the patient's body. The stem 20 may extend proximally and connect to a rotation controller outside the patient's body. The rotation controller may allow the physician to apply controlled rotation to the stem 20 and measures the amount of rotation of the stem 20. Since the distance between the two plates is proportional to the number of rotations, the extent of expansion of the medical device 10 can be easily determined and controlled. The rotation controller may have a display which shows the amount of rotation and the extent of expansion between the first plate 30 and the second plate 40.

The medical device 10 may comprise a number of radiopaque markers to indicate the location and position of the medical device 10 within the body and also the extent of expansion between the first plate 30 and the second plate 40.

The first plate 30 comprises a first radiopaque marker 32 at the distal end and a second radiopaque marker 33 at the proximal end. The first and second radiopaque markers 32, 33 allow a physician to visualise and identify the location of the medical device 10 within the patient's body. The first and second radiopaque markers 32, 33 also indicate the distal and proximal ends of the first plate 30 and therefore allow the physician to identify the working surface of the first plate 30. This allows a physician to more accurately place the device 10 within the target vessel.

The second plate 30 also comprises a first radiopaque marker 42 and a second radiopaque marker 43 which allow the physician to identify the location of the working surface of the second plate 40.

The physician would also be able to visually determine the distance between the first radiopaque marker 32 of the first plate 30 and the first radiopaque marker 42 of the second plate 40 under fluoroscopy. This would therefore allow a determination of the distance between the two plates 30, 40 to be made.

Figure 2:
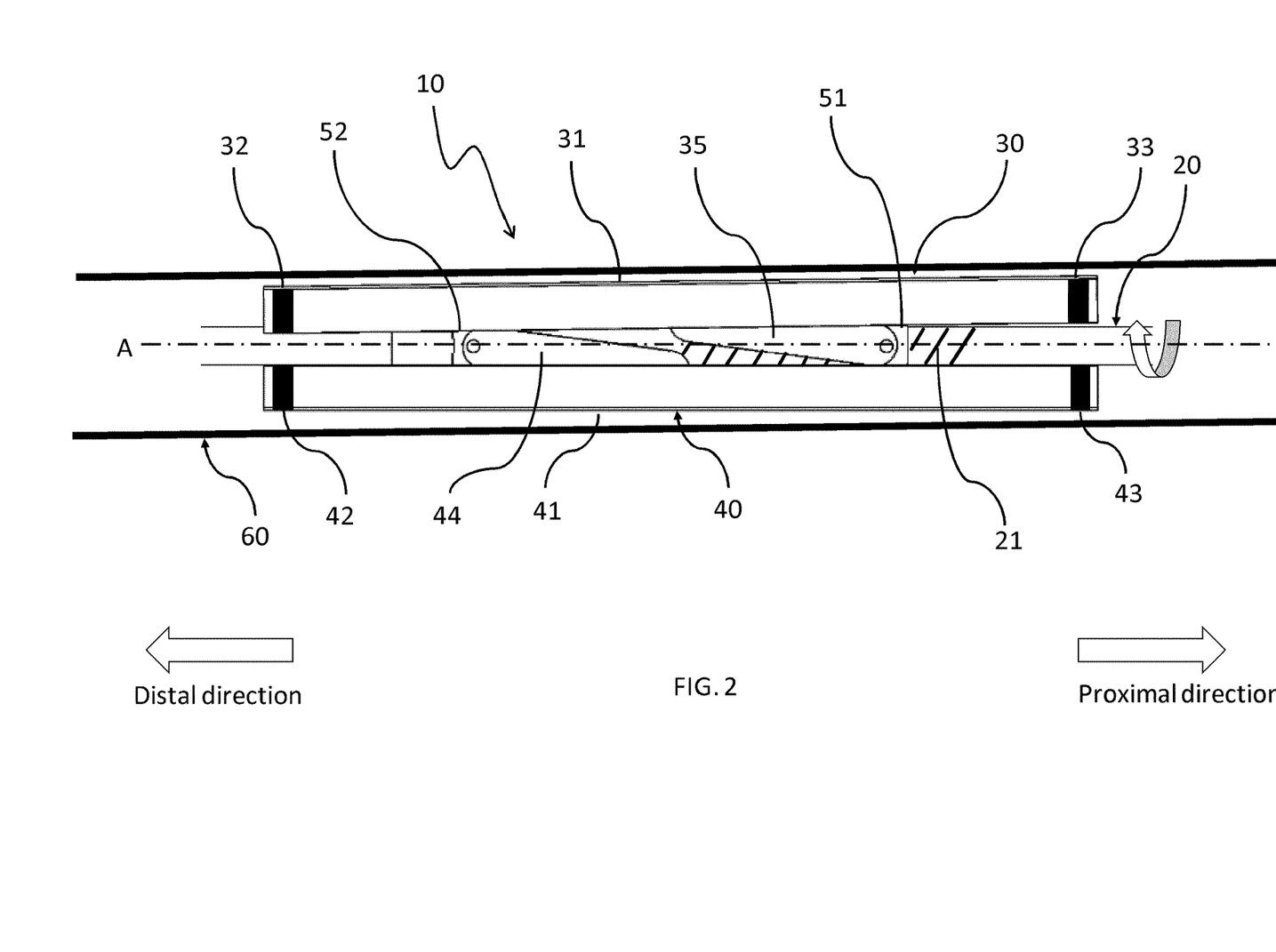
FIG. 2 shows a side view of the medical device of FIG. 1 in a collapsed configuration.

FIG. 2 shows a side view of the medical device 10 of FIG. 1 in a collapsed configuration, disposed within a catheter 60. In the collapsed configuration of FIG. 2 the moveable connector 51 is moved further proximally so that the distance between the fixed connecter 52 and the moveable connector 51 is greater than in the expanded configuration. The radial extent of the medical device 10 in the collapsed configuration is smaller than in the expanded configuration shown in FIG. 1.

The smaller radial extent allows the medical device to be disposed within the bore of the catheter 60 which is then introduced into a patient's blood vessel through an access site. The catheter 60 is navigated through the blood vessels of the patient using fluoroscopy, for example, to the target vessel which is to be dilated. Once the medical device 10 is located at the target vessel, the medical device 10 can be deployed by pulling back the catheter 60. The exact location of the medical device 10 can then adjusted by using the radiopaque markers 32, 33, 42, 43 disposed on the first plate 30 and second plate 40 to ensure that the working surface of the plates 30, 40 is aligned with the target site.

The medical device 10 can then be expanded from the collapsed configuration to the expanded configuration by rotating the stem 20 in a first direction. The first plate 30 and the second plate 40 will expand radially outwards and engage the inside surface of the vessel wall to apply a force to the inside of the vessel wall and dilate the vessel. The ridges 31, 41 provide focus points through which a greater force is applied to the vessel wall and highly calcified vessels can be cracked and dilated.

Once the vessel is sufficiently dilated, rotation of the stem 20 in a second direction will collapse the medical device 10 from the expanded configuration to the collapsed configuration. The catheter 60 can then be slid over the plates 30, 40 of medical device 10 and the catheter 60 together with the medical device 10 can be pulled proximally to remove it from the patient's body.

Figure 3A:
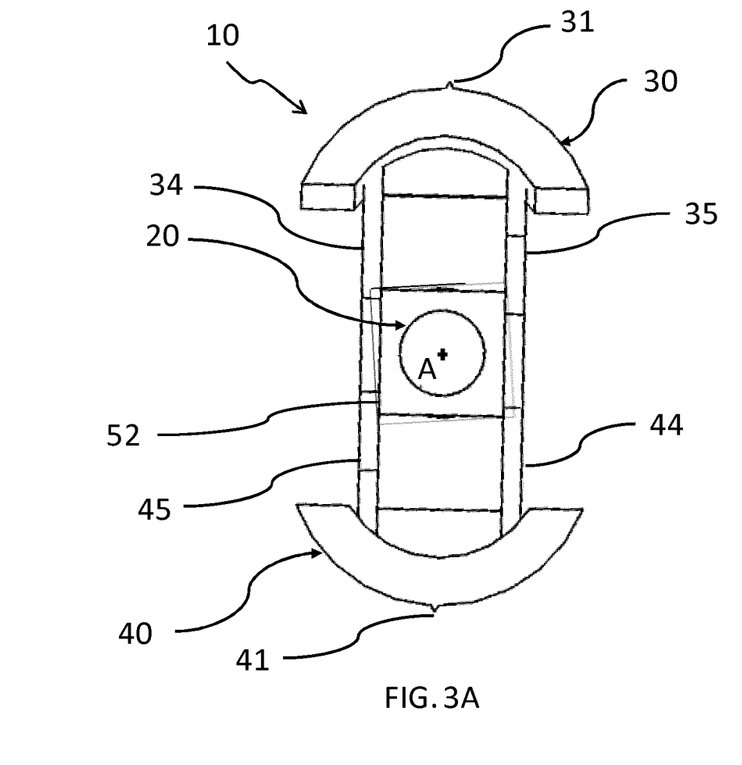
FIG. 3 shows frontal views of the medical device of FIG. 1 in an expanded configuration and a collapsed configuration.
Figure 3B:
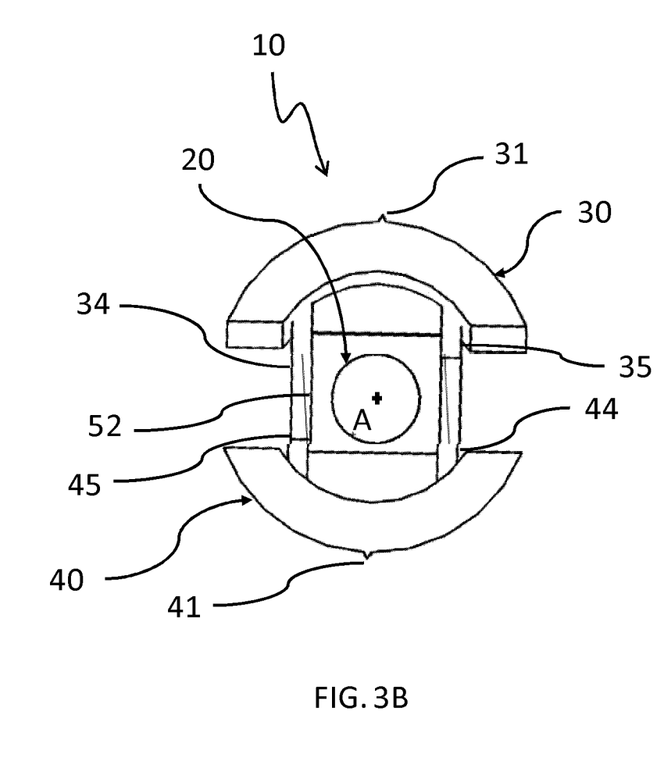

FIG. 3A shows a front view of the medical device 10 of FIG. 1 from the distal end in the expanded configuration. FIG. 3B shows a front view of the medical device 10 of FIG. 1 from the distal end in the collapsed configuration.

FIG. 3 illustrates that radial extent of the medical device 10 in the expanded configuration is greater than in the collapsed configuration.

The cross-sectional shape of the first plate 30 is the arc of a circular sector. The second plate 40 has the same cross-sectional shape and is disposed opposite the first plate 30.

The ridges 31, 41 are disposed centrally on the radial outside of the first and second plate 30, 40, respectively. The ridges may also be disposed off-centre.

The ridges 31, 41 are shown to have a triangular cross-sectional shape. However, the shape of the ridges is not limited to that shown in FIG. 3, as the ridges 31, 41 can take a number of different shapes such as, for example, triangular, rounded, rectangular or a knife edge shape.

FIG. 3 also illustrates that the first connection strut 34 and the second connection strut 35, connecting the first plate 30 to the stem 20, are radially offset in opposite directions from the stem to provide greater stability when expanding and collapsing the medical device 10.

Similarly, the third connection strut 44 and the fourth connection strut 45, connecting the second plate 40 to the stem 20, are also radially offset in opposite directions from the stem 20.

Figure 4:
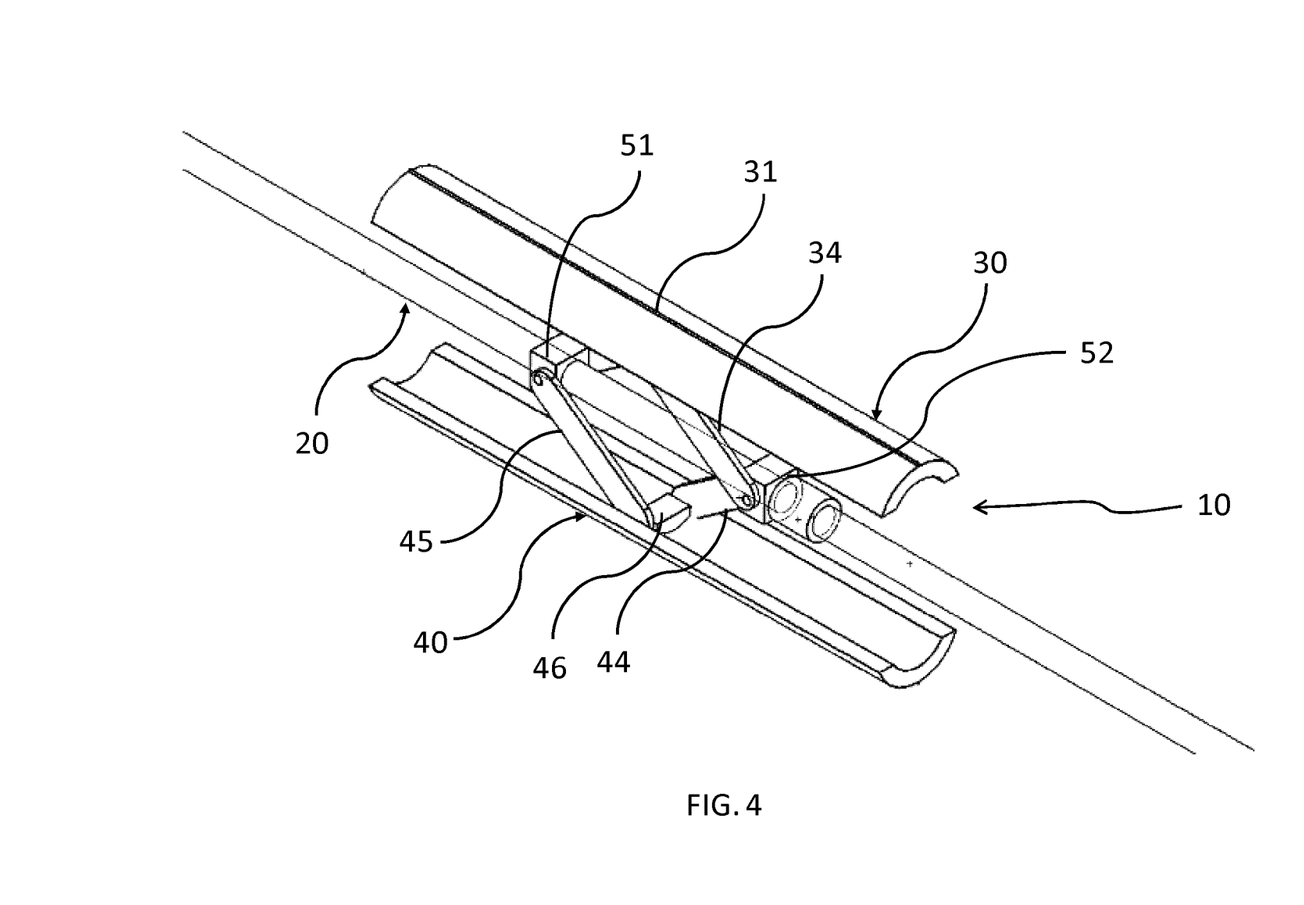
FIG. 4 shows an isometric view of the medical device of FIG. 1.

FIG. 4 shows an isometric view of the medical device 10 of FIG. 1 and illustrates more clearly how the components of the medical device 10 are arranged and connected in space. For example, the position and extent of the first ridge 31 can be seen to extend centrally and longitudinally along the length of the first plate 30.

FIG. 4 also shows one means by which the third connection strut 44 and the fourth connection strut 45 are attached to the inside surface of the second plate 40 using a connection block 46. The third connection strut 44 is connected on one side of the connection block 46 using a joint and the fourth connection strut 45 is connected on the opposite side of the connection block 46 using a joint such that the two connection struts are radially offset. The first connection strut 34 and second connection strut 35 are connected to the first plate 30 in the same manner.

Figure 5:
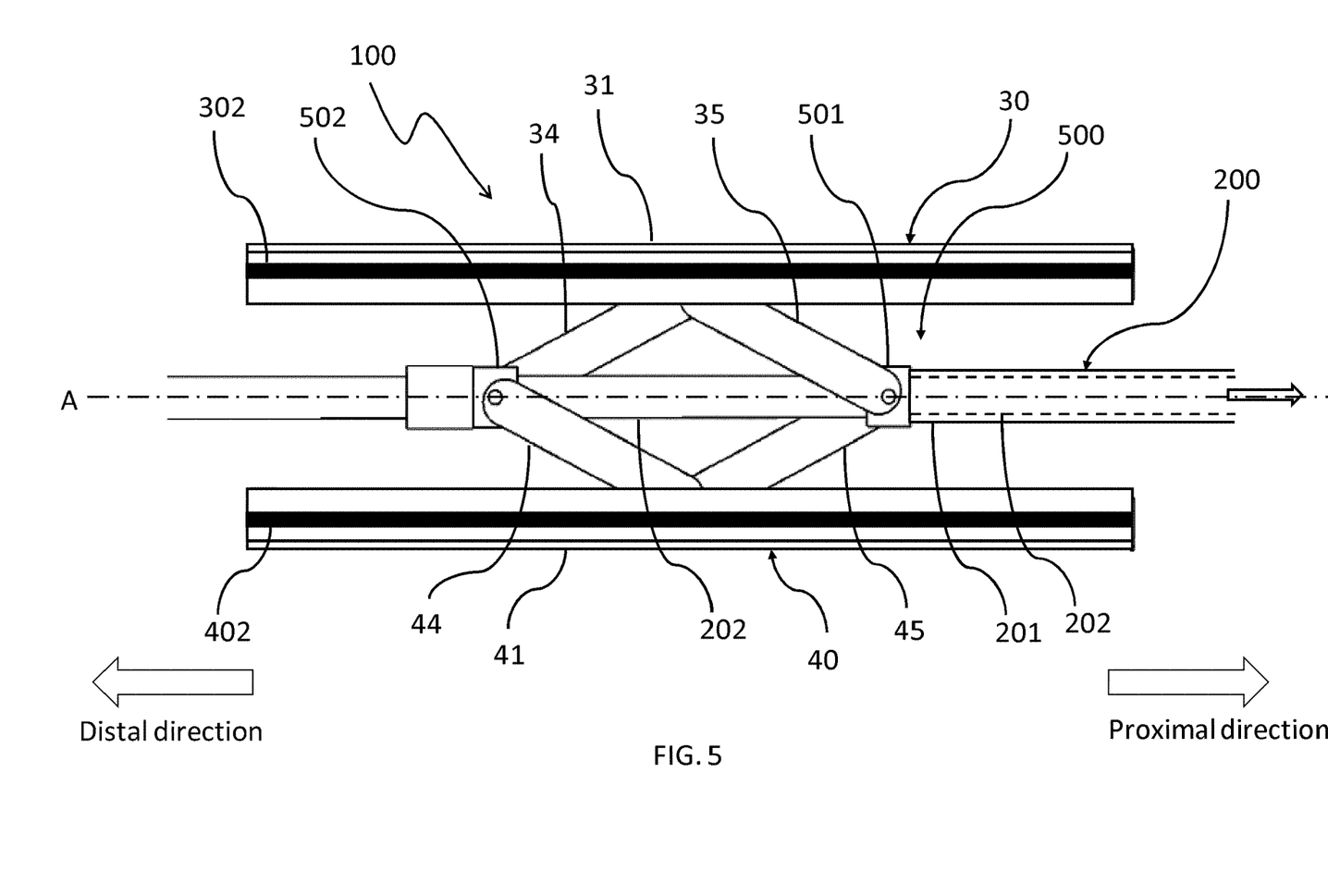
FIG. 5 shows a side view of a second embodiment of a medical device for dilating an endovascular lumen in an expanded configuration according to the present disclosure.

FIG. 5 shows a side view of a medical device 100 for dilating an endovascular lumen in an expanded configuration according to an alternative embodiment of the present disclosure.

The medical device 100 is similar to the medical device 10 of FIG. 1 and identical components are labelled with identical reference signs. However, the medical device 100 comprises an alternative expansion mechanism 500.

Like medical device 10 of FIG. 1, medical device 100 comprises a first plate 30 and a second plate 40 disposed on opposite sides of a stem 200. Each plate 30, 40 comprises a respective longitudinally extending ridge 31, 32. Medical device 100 also comprises a first connection strut 34 and second connection strut 35 which connect the first plate 30 to the central stem 200. A third connection strut 44 and a fourth connection strut 45 connect the second plate 40 to the stem 200.

However, unlike the medical device 10, the medical device 100 does not comprise a threaded portion on the stem 20 which engages with the movable connector 52. Rather, the stem 200 comprises a tubular portion 201 and a pull wire 202. The pull wire 202 is disposed within the bore of the tubular member 201 and extends distally from the tubular member 201.

A first connector 501 is fixed to the tubular member 201 such that it does not move longitudinally relative to the tubular member 201. The second connection strut 35 and the fourth connection strut 45 are rotatably connected to the first connector 501 through hinges or joints. A second connector 502 is fixed to the pull wire 202 such that it does not move longitudinally relative to the pull wire 202. The first connection strut 34 and the third connection strut 44 are rotatably connected to the second movable connector 502 through hinges or joints.

The pull wire 202 can move longitudinally relative to the tubular member 201. Since the first connector 501 and the second connector 502 are fixed to the tubular member 201 and the pull wire 202, respectively, relative longitudinal movement between the tubular member 202 and the pull wire 201 will result in longitudinal movement of the first connector 501 relative to the second connector 502. This relative movement of the connectors 501, 502 results in movement of the first and second plates 30, 40, radially inwards and outwards.

When the pull wire 201 is pulled in a proximal direction relative to the tubular member 202, the plates 30, 40 will move radially outwardly and the medical device 100 will expand from a collapsed configuration to an expanded configuration. On the other hand, when the tubular member 201 is pulled in a proximal direction relative to the pull wire 201, the plates will move radially inwardly and the medical device 100 will collapse from the expanded configuration to the collapsed configuration. The pulling of the pull wire 201 can be done by a physician outside the patient's body. Since the amount that the pull wire 201 is pulled corresponds to the amount of expansion of the medical device 100, this provides a simple yet accurate means of controlling the extent of expansion of the medical device 100.

Alternatively, the medical device 100 may have a hydraulic actuator as part of the expansion mechanism. The hydraulic actuator may be remotely controlled to move the first connector 501 and the second connector 502 relative to each other and hence move the first and second plates 30, 40 radially outwards and inwards. The hydraulic actuator could be disposed between the first connector 501 and the second connector 502 or disposed at a proximal end of the device 100.

The medical device 100 of FIG. 5 also shows an alternative arrangement of radiopaque markers. This arrangement of radiopaque markers is not limited to the embodiment of medical device 100. The medical device 100 may have the same arrangement of radiopaque markers as medical device 10 and vice versa.

The first plate 30 comprises a first radiopaque marker 302 extending along the longitudinal length of the first plate 30. The second plate 40 also comprises a first radiopaque marker 402 extending along the longitudinal length of the second plate 40. The radiopaque marker 302 and 402 are each able to indicate the length of the device 100 and therefore assist with locating and positioning of the device 100 within the target vessel. Furthermore, the distance between radiopaque marker 302 and radiopaque marker 402 corresponds to the distance between the first plate 30 and second plate 40. The distance between these two markers therefore allows the physician to determine the extent of expansion of the device 100.

Figure 6:
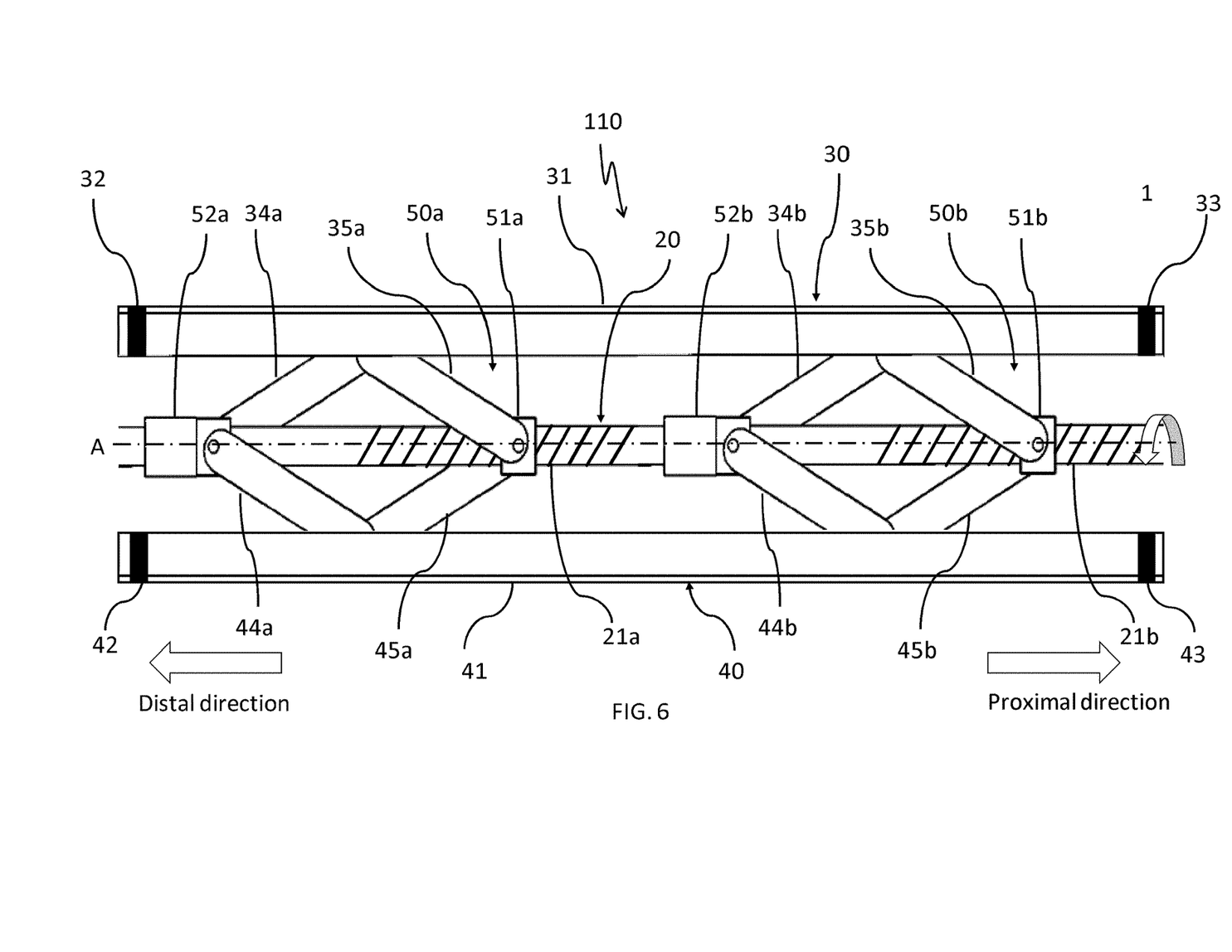
FIG. 6 shows a side view of a third embodiment of a medical device for dilating an endovascular lumen in an expanded configuration according to the present disclosure.

FIG. 6 shows a side view of a medical device 110 in an expanded configuration according to an alternative embodiment of the present disclosure.

The medical device 110 is similar to the medical device 10 of FIG. 1 but it comprises two expansion mechanisms 50a and 50b disposed in series on the same stem 20 and connected to the same first plate 30 and second plate 40.

Each expansion mechanism comprises a separate fixed connector 52a, 52b, a separate moveable connector 51a, 51b, a separate threaded portion 21a, 21b and four separate connection struts 34a, 35a, 44a, 45a, and 34b, 35b, 44b, 45b. Each expansion mechanism 50a, 50b, functions in the same manner as described with reference to FIG. 1 above. However, both expansion mechanisms are controlled through rotation of the same stem 20 and therefore rotation of the stem in a first direction will cause uniform expansion of both expansion mechanism 50a, 50b and the first and second plates 30, 40 to move radially outwardly. Similarly, rotation of the stem 20 in a second direction will result in uniform collapse of both expansion mechanism 50a, 50b and the first and second plate 30, 40 to move radially inwards.

Using multiple expansion mechanisms connected in series allows a longer length of plates 30, 40 to be supported. The multiple expansion mechanisms provide a more evenly distributed expansion force along the plates 30, 40 and the medical device 110 is therefore useful for treating target vessels with longer target sites.

The expansion mechanisms 50a, 50b can also be replaced by two of the pull wire expansion mechanisms 500 of FIG. 5 disposed in series.

Figure 7:
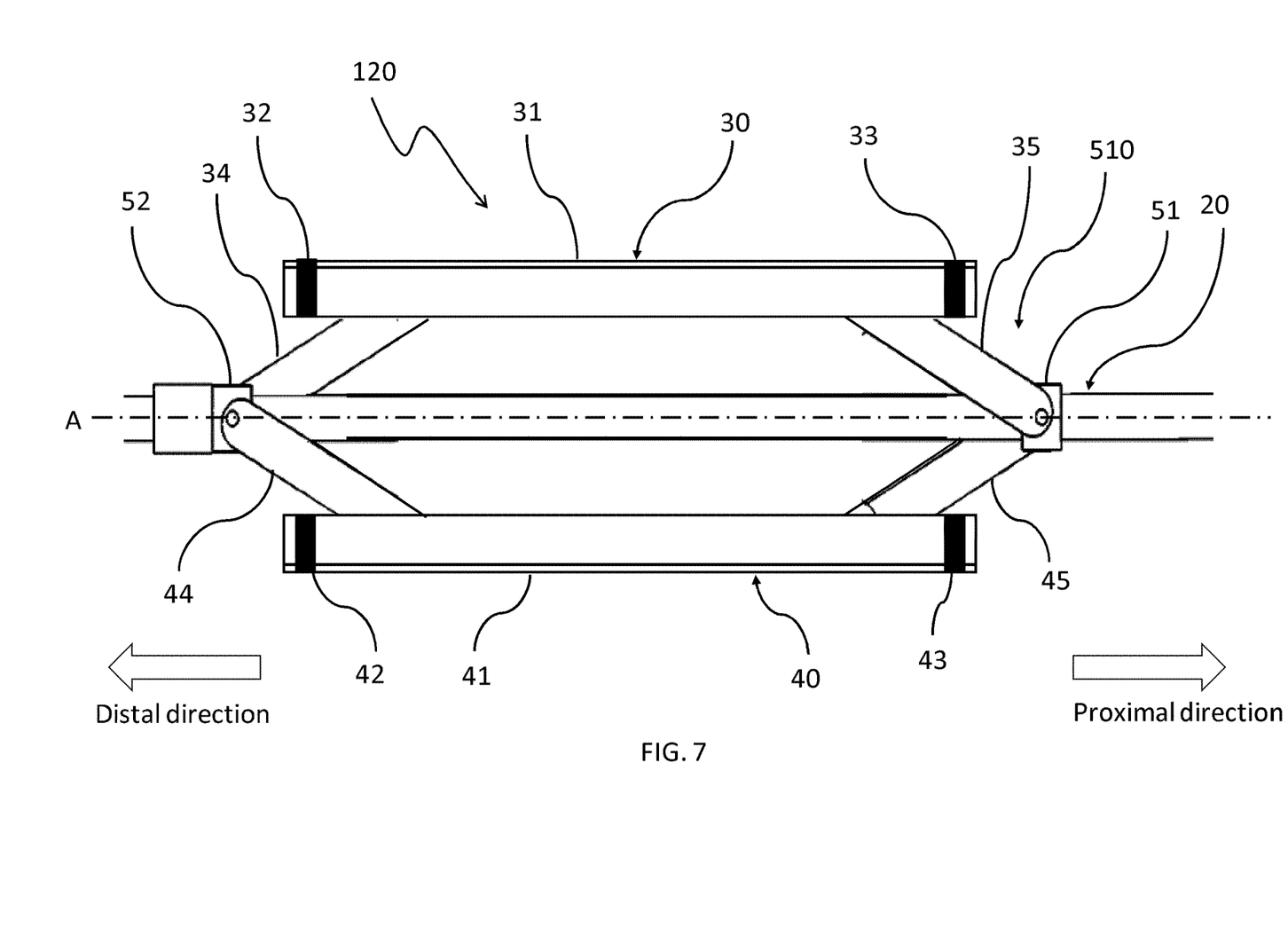
FIG. 7 shows a side view of a fourth embodiment of a medical device for dilating an endovascular lumen in an expanded configuration according to the present disclosure.

FIG. 7 shows a side view of a medical device 120 in an expanded configuration according to an alternative embodiment of the present disclosure.

The medical device 120 of FIG. 7 shows an alternative arrangement for the expansion mechanism 510. The individual components such as the fixed connector 52, movable connector 51 and connection struts 34, 35, 44, 45 are identical to the ones described with reference to the other figures. However, the movable connector 51 and the fixed connector 52 are longitudinally spaced apart such that the fixed connector is positioned closer to the distal end of the device and the moveable connector 51 is positioned closer to the proximal end of the device 100. The first connection strut 34 which is connected to the fixed connector 52 is also longitudinally spaced apart from the second connection strut 35 which is connected to the moveable connector 51. The first and second connection struts 34, 35 do not attach to the same point on the first plate 30 anymore. Similarly, the third connection strut 44 and fourth connection strut 45 also do not attach to the same point on the second plate 40.

This results in two points on each of the first plate 30 and second plate 40 where a connection strut is connected and therefore two points where a force from the expansion mechanism 510 is applied to the plate 30, 40. This therefore results in a more uniform application of force from the expansion mechanism 510 to the plates 30, 40 and more uniform expansion of the first and second plates 30, 40.

The medical device 120 may use either the threaded rotary expansion mechanism of FIG. 1, the pull wire mechanism of FIG. 5 or the hydraulic actuator mechanism.

The invention is not limited to the above-described embodiments. Various modifications are possible. For example, the medical device is not limited to having two plates which are disposed opposite each other. The medical device may, for example, have three plates angularly displaced at 120 degrees from each other. The medical device may also have more than three plates disposed at different angular positions.

Only one of the plates may be moveable. The other plate may be fixed relative to the stem and may not move radially inwards or outwards.

The medical device may have one, two or more expansion mechanisms disposed in series.

A number of different actuation mechanisms may be used to expand and collapse the medical device 100. For example, the threaded rotary mechanism, the pull wire mechanism or the hydraulic actuator mechanism may be used interchangeably.

The connection struts 34, 35, 44, 45 may be arranged in a number of different ways. For example, the connection struts may not be radially offset from each other. The device 100 may comprise more than four connection struts.

The connector 51 and connection struts 35, 35, and the connector 52 and connection struts 34, 44 may be disposed in opposite relation to each other such that movement of the connector 51 and connector 52 away from each other results in movement of the plates radially outwardly and the device expanding, while movement of the connector 51 and the connector 52 towards each other results in movement of the plates radially inwardly and the device collapsing.

The first and/or second plate 30, 40 may have a variety of different shapes. For example, the first and/or second plate 30, 40 may be flat, they may be comprised of a number of straight-line segments, they may be curved about the longitudinal axis or they may have a cross section of a circular segment.

The first plate 30 may be a different shape from the second plate 40. The first plate 30 may have a different longitudinal length from the second plate 40.

Each of the first and/or second plate 30, 40 may have no ridge, one ridge or multiple ridges. The ridge or ridges 31, 41 may extend along the full longitudinal length of the plate or only along part of the longitudinal length of the plate.

The ridge or ridges 31, 41 may have a number of different shapes such as, for example, a triangular shape, a rounded shape, a circular shape, a knife edge shape or a rectangular shape.

The ridge or ridges 31, 41 may extend longitudinally along the plate or they may take other patterns such as, for example, extending circumferentially around the plate, extending diagonally along the plate or extending in a helix pattern along the plate.

Each of the first and second plates 30, 40 may have none, one or multiple radiopaque markers in a variety of shapes disposed on it. For example, each plate may have multiple radiopaque markers disposed at regular intervals on the plate.

The radiopaque marker or markers may be circumferentially, longitudinally or diagonally extending along the plates 30, 40.

The entire first and/or second plate 30, 40 may be made from a radiopaque material.

The stem 20 may have one or more radiopaque markers disposed thereon.

All of the above are fully within the scope of the present disclosure and are considered to form the basis for alternative embodiments in which one or more combinations of the above described features are applied, without limitation to the specific combination disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptations fall within the scope of the present disclosure.

The invention claimed is:

1. A medical device for dilating an endovascular lumen and having a collapsed configuration and an expanded configuration, the medical device comprising:
   a stem extending along a longitudinal axis of the medical device;
   a first plate disposed partly around the stem;
   a second plate disposed partly around the stem angularly separated in a circumferential direction from the first plate; and
   an expansion mechanism configured to move each of the first plate and/or the second plate radially outwardly when the medical device is expanded from the collapsed configuration to the expanded configuration,
   wherein each of the first plate and/or the second plate comprises at least one ridge disposed on a radial outside surface of the plate, the at least one ridge includes a focus point that extends along a longitudinal length in a longitudinal direction and along a circumferential length in the circumferential direction, and wherein the longitudinal length is longer than the circumferential length, and
   wherein each of the first plate and/or the second plate is connected to the stem using at least two connection struts.

2. The medical device of claim 1, wherein the expansion mechanism is a mechanically driven leverage mechanism.

3. The medical device of claim 1, wherein the expansion mechanism is configured to move each of the first plate and/or the second plate radially outwardly by moving the at least two connection struts relative to each other.

4. The medical device of claim 1, wherein the at least two connection struts each comprise a first end and a second end, and wherein the first ends are connected to the stem and the second ends are connected to the plate.

5. The medical device of claim 4, wherein the expansion mechanism is configured to move the first ends of the at least two connection struts relative to each other to move each of the first plate and/or the second plate radially outwardly.

6. The medical device of claim 1, wherein the at least two connection struts comprise a first connection strut and a second connection strut.

7. The medical device of claim 6, wherein a first end of the first connection strut is fixed to the stem to restrict longitudinal movement of the first end relative to the stem.

8. The medical device of claim 7, wherein the expansion mechanism is configured to move the first end of the first connection strut and the first end of the second connection strut towards each other to cause the first and second plates to move radially outwardly when the medical device is expanded from the collapsed configuration to the expanded configuration.

9. The medical device of claim 6, wherein a first end of the second connection strut is movably connected to the stem such that the first end can move longitudinally relative to the stem.

10. The medical device of claim 1, wherein the second plate is disposed opposite the first plate.

11. The medical device of claim 10, wherein the expansion mechanism is configured to move the plates radially outwardly in opposite directions when the medical device is expanded from the collapsed configuration to the expanded configuration.

12. The medical device of claim 1, wherein the expansion mechanism comprises the stem having a tubular member and a pull wire.

13. The medical device of claim 1, wherein the expansion mechanism comprises a hydraulic actuator.

14. The medical device of claim 13, wherein actuation of the hydraulic actuator will cause the at least two connection struts to move relative to one another.

15. The medical device of claim 13, wherein actuation of the hydraulic actuator will cause each of the first plate and/or the second plate to move radially outwardly and the medical device to expand from the collapsed configuration to the expanded configuration.

16. The medical device of claim 1, wherein the at least one ridge extends longitudinally along each of the first plate and/or the second plate.

17. A medical device for dilating an endovascular lumen and having a collapsed configuration and an expanded configuration, the medical device comprising:
   a stem extending along a longitudinal axis of the medical device;
   a first plate disposed partly around the stem;
   a second plate disposed partly around the stem angularly separated in a circumferential direction from the first plate; and
   an expansion mechanism configured to move each of the first plate and/or the second plate radially outwardly when the medical device is expanded from the collapsed configuration to the expanded configuration,
   wherein each of the first plate and/or the second plate comprises at least one ridge disposed on a radial outside surface of the plate, the at least one ridge includes a focus point that extends at least partially along the longitudinal axis, the ridge extends along the full longitudinal length of the first plate and/or the second plate, and wherein each of the first plate and/or the second plate is connected to the stem using at least two connection struts.

* * * * *